United States Patent [19]

Green et al.

[11] Patent Number: 5,286,835
[45] Date of Patent: Feb. 15, 1994

[54] PREPARATION OF VINYL ETHER TERMINATED POLYESTERS

[75] Inventors: George D. Green, Park Ridge; James R. Snyder, Chicago; Darryl K. Barnes, Bellwood, all of Ill.

[73] Assignee: Allied-Signal Inc., Morris Township, Morris County, N.J.

[21] Appl. No.: 935,078

[22] Filed: Aug. 24, 1992

[51] Int. Cl.⁵ .............................................. C08G 63/47
[52] U.S. Cl. ..................................... 528/272; 528/274; 528/300; 528/301; 528/308; 528/392; 525/438; 525/445; 525/447; 560/91; 560/198
[58] Field of Search ............... 528/272, 274, 300, 301, 528/308, 392; 525/438, 445, 447; 560/91, 198

[56] References Cited

U.S. PATENT DOCUMENTS

| | | | |
|---|---|---|---|
| 4,749,807 | 6/1988 | Lapin et al. | 560/91 |
| 4,775,732 | 10/1988 | Lapin | 528/49 |
| 4,845,265 | 7/1989 | Lapin | 560/84 |

*Primary Examiner*—John Kight, III
*Assistant Examiner*—Sam A. Acquah
*Attorney, Agent, or Firm*—Harold N. Wells; Roger H. Criss; Mary Jo Boldingh

[57] ABSTRACT

Vinyl ether terminated ester oligomers having a range of molecular weights are prepared by reacting a vinyl ether terminated polybasic ester with a polyol in the presence of a catalyst. Continual removal of a hydroxy monovinyl ether avoids formation compounds containing acetal moieties. Alternatively, a polybasic ester is chain extended with a polyol with continual removal of the alcohol by-product. Then, the terminal ester moieties are end capped with a monohydroxy vinyl ether. The oligomers have application in coatings and the like.

17 Claims, No Drawings

PREPARATION OF VINYL ETHER TERMINATED POLYESTERS

BACKGROUND OF THE INVENTION

The invention is related to vinyl ether ester oligomers useful for coatings and related applications. More particularly, it relates to new methods of preparing such oligomers which provide a range of useful molecular weight materials.

Vinyl ether ester oligomers are disclosed in a group of U.S. Pat. Nos. assigned to Allied-Signal Inc., namely U.S. Pat. Nos. 4,749,807, 4,775,732, and 4,845,265. These patents disclose methods for making the vinyl ether ester oligomers which are not considered commercially useful in preparing oligomers. Where acid chlorides are used, the oligomer contains HCl which must be removed. Where esters are used, the vinyl ethers may be converted in substantial amounts to compounds having an acetal moiety, preventing higher molecular weight oligomers from being formed and potentially interfering with the formation of polymers in subsequent processing. Consequently, new methods for producing vinyl ether ester oligomers have been sought by the present inventors and their improved methods will be disclosed below.

SUMMARY OF THE INVENTION

The invention makes possible vinyl ether terminated ester oligomers having a range of molecular weights while avoiding the formation of acetal moieties. The process may be generally characterized as being a sequential one in which an ester is reacted with a polyol and the molecular weight of the oligomers produced is adjusted by varying the initial ratio of ester to polyol and in which the by-products are continually vaporized and removed.

In one embodiment, a vinyl ether terminated polybasic ester is reacted with a polyol in the presence of a transesterification catalyst to produce a vinyl ether terminated oligomer of the polybasic acid and the polyol. The principal by-product of the reaction is a hydroxy monovinyl ether which is removed by distillation during the reaction. Substantially all of the hydroxy monovinyl ether can be recovered and optionally may be subsequently converted to one of the starting materials by reaction with a polybasic ester. In another embodiment, a polybasic ester is chain extended with a polyol in the presence of a transesterification catalyst and thereafter a hydroxy monovinyl ether is added to cap the ends of the oligomer. The loss of vinyl ether and ester to by-products containing acetal moieties characteristic of the prior art processes is avoided, making possible the preparation of oligomers having a range of molecular weights and having important applications in radiation-curable coatings and for related applications. Thermal curing is also possible.

The process is carried out at elevated temperatures and under a vacuum suitable for the reactants. Typically temperatures in the range of about 50° C. to 250° C. and a vacuum in the range of 0.01 to 500 torr (0.0013 to 66.7 kPa.abs.) will be used. The mol ratio of the ester to polyol will be chosen to provide the desired molecular weight product generally 1/20 to 20/1, preferably between 1/5 to 5/1. Most preferably about 1.5/1 to 1/1.5, but excluding a ratio of exactly 1.0/1.0.

In one representative embodiment a difunctional vinyl ether-terminated polybasic ester such as the product of the reaction of dimethyl isophthalate (DMI) with cyclohexane dimethanol monovinyl ether (CHDMVE) is reacted with a polyol, such as a polytetrahydrofuran, in the presence of a catalyst such as dibutyl tin diacetate at an elevated temperature under vacuum, during which time CHDMVE is continually vaporized and removed. The recovered CHDMVE may be reacted with DMI to provide additional starting material.

In another representative embodiment, dimethylisophthalate (DMI) is chain extended by reaction with a polytetrahydrofuran in the presence of the dibutyl tin diacetate catalyst at an elevated temperature under vacuum while methanol is continually vaporized and removed. Thereafter, cyclohexane dimethanol monovinyl ether (CHDMVE) is added to cap the terminal ester groups.

DESCRIPTION OF THE PREFERRED EMBODIMENTS

Reactants
Polybasic esters
The polybasic esters useful in the invention may be described by the formula

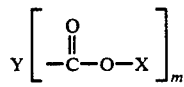

where
- Y is a radical having a molecular weight of 14 to above 500 and selected from the group consisting of alkylene, arylene, aralkylene and cycloalkylene radicals
- X is a radical selected from the group consisting of alkyl having 1 to 6 carbon atoms, arylene, and aralkylene
- m is 2 to 6.

Examples of the alkylene moieties which may be used include methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene, nonadecylene, and eicosylene. Examples of arylene groups include phenylene, naphthylene, anthrylene, and phenanthrylene. Cycloalkylene groups include the cyclopentylene, cyclohexylene, cycloheptylene, cyclooctylene, and cycloalkylene groups containing 1 or more alkyl groups on the nucleus. Similarly, the arylene groups which may be used for Y also may contain one or more alkyl groups on the aromatic ring, especially where such alkyl groups contain up to about 6 carbon atoms. Examples of aralkylene groups include benzylene, 1-phenethylene, 2-phenethylene, 3-phenylpropylene, 2-phenylpropylene, 1-phenylpropylene, etc. Particularly useful Y groups are —(CH$_2$)$_n$— groups where n is 1 to 4; 1,2, 1,3, or 1,4 phenylene groups; and 1,4-cyclohexylene groups, such as 1,4-cyclohexane (cis/trans), dimethylphthalate, dimethylisophthalate, dimethylterephthalate, and 1,5, 2,6-naphthylene dicarboxylate.

Particularly useful X groups are methyl, ethyl, propyl, butyl, isopropyl, isobutyl, phenyl, p-nitrophenyl, p-chlorophenyl.

Alternatively, tri or tetra basic esters may be used. In such cases the moiety Y is typically an aralkylene group. Examples include 1,2,4-trimethyl benzene tricarboxylate, 1,3,5-trimethyl benzene tricarboxylate, and 1,2,4,5-tetra-methyl benzene tetracarboxylate, 3,3',4,4'-tetra-methyl benzophenone tetracarboxylate, 1,4,5,8-tetra-methyl naphthalene tetra carboxylate, and bicyclo[2.2.1]heptane tetramethyl-tetracarboxylate.

Hydroxyl Monovinyl Ethers

The vinyl ether terminated alcohols which are used in preparing the oligomeric esters of this invention have a structure corresponding to the adduct of an alkyne and a diol. However, these vinyl ether terminated alcohols also can be made in other ways, and the method of producing them is not part of this invention. The alkyne has the generic formula R'C≡CR", and the diol has the generic formula HO—Z—OH. The generic formula of the vinyl ether terminated alcohols of our invention then is

R'CH=CR"O—ZOH

The groups R' and R" are independently selected from the group consisting of hydrogen and lower alkyl moieties containing from 1 to 10 carbon atoms, although those with from 1 to about 4 carbon atoms are favored. It is preferable that both R' and R" are not alkyl moieties, for in the case where both are lower alkyl groups this causes an undesirable reduction in polymerization rate of the oligomers of our invention. Where R' is an alkyl moiety it is preferred that R" be hydrogen, and conversely; where R' is hydrogen then R" should be an alkyl of 1 to 4 carbons. In a preferred embodiment R' or R" is a methyl group and R" and R' is hydrogen. In a still more preferred embodiment both R' and R" are hydrogen.

Z will be a divalent radical havig a molecular weight of 28 to about 500 and selected from the group consisting of alkylene or cycloalkylene radicals.

Among the diols one important class consists of alkylene glycols, HO($C_nH_{2n}$)OH, where n is an integer from 2 to about 10. The linear alkylene glycols, HO(CH$_2$)$_n$OH, (polymethylenediols), where n is an integer from 2 to about 10, are particularly useful, especially where n is from 2 to about 6. Illustrative of the members of this group are such diols as ethylene glycol, 1,3-propylene glycol, 1,4-butanediol, 1,5-pentanediol, 1,6-hexanediol, 1,7-heptanediol, 1,8-octanediol, 1,9-nonanediol, and 1,10-decanediol.

The nonlinear or branched alkylene diols also may be used, where such glycols contain from 3 up to about 10 carbon atoms. Examples include 1,2-propylene glycol, 2,3-butanediol, 2,3-dimethyl-2,3-butanediol, 2,3-dimethyl-1,4-butanediol, 2,2-dimethyl-1,3-propanediol(-neopentylglycol).

Another useful class of diols are the polyalkylene glycols, especially poly(ethylene) glycols, HO-[—CH$_2$CH$_2$O—]$_m$H, and poly(polypylene) glycol, HO-[—CH(CH$_3$)CH$_2$O—]$_m$H, where m is an integer from 1 up through about 50, although more usually m is an integer from 1 up to about 10, and most preferably from 1 up to about 5. Examples of these glycols include diethylene glycol, triethylene glycol, tetraethylene glycol, pentaethylene glycol, and hexaethylene glycol, along with the analogs of the propylene glycols.

Of particular importance is the case where Z is a divalent radical whose parent is a cycloalkane, such as cyclopentane, cyclohexane, cycloheptane, or cyclooctane, preferably the bishydroxy alkyl derivatives. The preferred diols are the 1,3-bis(hydroxyalkyl)cyclopentanes and the 1,4-bis(hydroxyalkyl)cyclohexanes, -cycloheptanes, and -cyclooctanes, particularly the cyclohexanes. The bis(hydroxymethyl)cyclohexanes are preferred as they are available from the reduction of the corresponding phthalic acids, and among these 1,4-bis(-hydroxymethyl)cyclohexane is favored.

Of the hydroxy monovinyl ethers which may be produced by the reaction of acetylene with the diols described above, those which are especially preferred include 4-hydroxybutyl vinyl ether, 4-hydroxymethyl cyclohexylmethyl vinyl ether, 2-hydroxy ethyl vinyl ether, triethylene glycol monovinyl ether, and diethylene glycol monovinyl ether.

Polyols

The polyols which may be used in the process of the invention include diols described above and higher polyols. They may be generally described by the formula A-[OH]$_n$ where:
n is 2 to 6,
A is a radical selected from the group consisting of linear or branched alkyl having 2 to 10 carbon atoms,
polyesters,
linear and cyclic ethers,
arylene, or
aralkylene.

The diols described above are examples of those which may be employed as polyols as well. Particularly preferred diols include 1,4-cyclohexane dimethanol (CHDM), 1,2-ethane diol (ethylene glycol) 1,3-propane diol, 1,4-butane diol, 1,5-pentane diol, 1,6-hexane diol, and 1,4-but-2-yne diol. Polyester diols may be derived from poly carboxylic acids such as adipic, isophthalic, succinic, for example, Formrez 11,22,33,44,55,66,23,24,61, 65,56,8005,8008,8009 (Witco Corp.). Polytetrahydrofuran diols are particularly useful, for example poly THF 250, 650, 1000, 2000 (BASF). Arylene derivatives such as 1,3-benzenedimethanol, 1,4-benzene dimethanol, 1,3-dihydroxybenzene, and 1,4-dihydroxybenzene are notable. Other include neopentyl glycol, propylene glycol, 1,3-α,α'-dihydroxyl tetramethyl xylene, and 1,4-α,α' dihydroxy tetramethyl xylene.

Preferred polyols include the Tone series such as 0301, 0305, 0310 derived from caprolactone and trimethylolpropane and available from Union Carbide, the Photonol series such as PhO-7149, PhO-7156, PhO-7158, derived from ethylene oxide and trimethylol propane and available from Henkel Corp., trimethylol propane, and pentaerythritol.

Catalysts

The catalysts useful in the process of the invention generally are transesterification catalysts. Examples of such catalysts include dibutyl tin diacetate, dibutyl tin dilaurate, titanium tetra isopropoxide, lead oxide, antimony oxide, manganese diacetate, cobalt diacetate hydrate, nickel diacetate hydrate, and lithium metal and mixtures thereof. The amount required will vary but generally will be about 0.005 to 0.5 wt. % based on oligomer product weight.

Stabilizers

Stabilizers are optionally used to prevent discloration and premature curing. Preferred materials include triphenyl phosphate, triphenyl phosphite, tinuvin 440

(Ciba-Geigy), Irganox 1035, 1010, 1076 (Ciba-Geigy), and KOH.

Reaction Conditions

Specific examples given below will provide typical conditions found useful in the process of forming vinyl ether terminated ester oligomers. More generally, the process may be described as a sequential one in which the molecular weight of the oligomers produced is adjusted by varying the initial ratio of the ester to the polyol and in which by-products are continually vaporized and removed. Preferably, the reaction conditions are adjusted so that neither the ester nor the polyol are removed.

There are two basic variations of the process. In one aspect, the process involves contacting of a vinyl ether-terminated polyester with a polyol, or alternatively, the reaction of a polyester with a hydroxy monovinyl ether to form the vinyl ether terminated polyester, followed by reaction with a polyol. A vinyl ether is produced by the chain extension reaction and separated immediately from the reacting mixture. An example employing a dibasic ester is as follows:

depending upon the temperature, concentrations, catalyst and other factors familiar to those skilled in the art.

In another aspect, the polybasic ester is chain extended with the polyol, followed by addition of a hydroxy monovinyl ether to cap the chain extended ester. This may be illustrated as follows:

Chain Extension of an Ester (III)

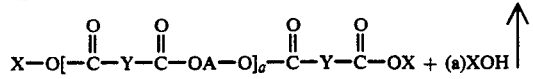

End Capping the Oligomer (IV)

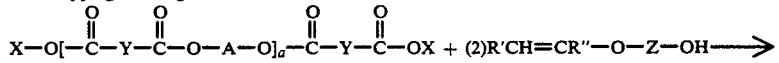

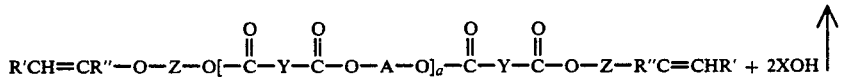

The first step, chain extension, will be carried out in the liquid phase at temperatures of about 50° to 250° C. and a vacuum selected to effectively remove alcohol (XOH), generally about 0.01 to 500 torr (0.0013 to 66.7 kPa.abs.). The reaction requires about 0.5 to 10 hours to complete, depending on the temperature, concentrations, catalyst, and other factors familiar to those skilled in the art. The alcohol formed as a by-product is continuously removed during the reaction.

The second step, end capping, will take place at temperatures of about 50° to 180° C. and a vacuum selected to efficiently remove alcohol, generally about 0.5 to 10 torr (0.0013 to 66.7 kPa.abs.). The reaction requires about 0.5 to 10 hours to complete, depending on various factors as suggested above. Again, alcohol is removed as formed.

Vinyl Ether Termination of an Ester (I)

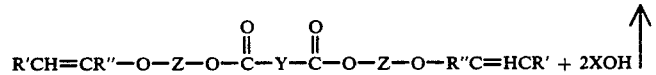

Chain Extension of the Vinyl Ether Terminated Ester (II)

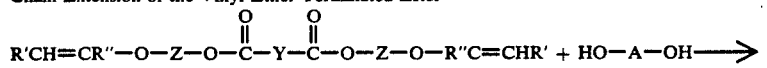

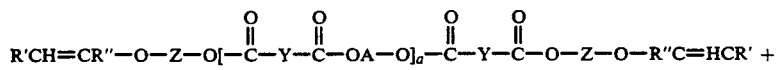

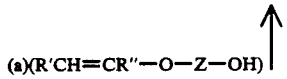

The reaction may be carried out in the liquid phase at temperatures in the range of about 50° to 250° C. and at a vacuum selected to permit efficient removal of the hydroxy monovinyl ether by-product, typically about 0.01 to 500 torr (0.0013 to 66.7 kPa.abs). In general, the reaction will require about 1 to 20 hours to complete, The objective of either reaction scheme is to provide a series of vinyl ether capped ester oligomers varying in molecular weight, viscosity, and reactivity. The molecular weight is generally controlled by the ratio of the ester to the polyol. As the mol ratio approaches 1.0/1.0 the molecular weight becomes undesirably high and consequently mol ratios of about 1.5/1 are preferred, however, only exactly equal amounts of the reactants are excluded and ratios between 1.5/1 and 1.0/1.0 may be used. As the mol ratio is raised still higher the product approaches a single molecule of the ester end capped with a vinyl ether (i.e. no polyol is present). Such materials are useful, but generally require the presence of higher molecular weight oligomers for most practical applications. Alternatively, increasing the polyol so that it is in excess of the ester, i.e. less than 1.0/1.0, will produce an oligomer terminated with hydroxyl groups, which must be terminated with a vinyl ether terminated ester. This alternative is feasible, but not preferred.

EXAMPLE 1

A 250 mL high temperature polycondensation flask equipped with a short path distillation sidearm was charged with polyTHF-1000 (polytetrahydrofuran BASF, OH #-114.8, 97.7 g, 0.20 mol OH), VEctomer ™ 4010 (reaction product of isophthallic acid and hydroxy butyl vinyl ether, Allied-Signal) (54.6 g, 0.15 mol) and dibutyl tin diacetate catalyst (5 drops). The flask was fitted with a mechanical stirrer and a vacuum applied (0.6 torr) (0.08 kPa.abs.). The mixture was stirred at 130° C. for two hours during which time 22.3 g (96% of theory) hydroxybutylvinyl ether (HBVE) was distilled from the reaction mass. The mixture was cooled to room temperature and used without further purification. FTIR indicates no detectable OH stretch and GPC (EtOAc solvent, RI detection) shows 5.1% free VEctomer ™ 4010. Molecular weights were calculated from the GPC data using polystyrene standards: $Mn = 5597$, $Mw = 16893$. HNMR analysis indicated only a trace of acetal formation. The lack of acetals is favorable to complete polymer network formation and avoids the potential for extractables caused by acetal cleavage.

EXAMPLE 2

The procedures of Example 1 were repeated with different proportions and starting materials. The results are summarized in the following table (including the results of Example 1).

TABLE A

| Test Number | OH terminated reagent | alcohol used, g (mol free OH) | VEctomer ™ 4010 Used, g (mol ester) | % Free 4010[5] | Mn[5] | Mw[5] |
|---|---|---|---|---|---|---|
| 1 | PolyTHF-1000 | 97.7 (0.2 mol OH) | 54.4 (0.3 mol ester) | 5.1% | 5596 | 16893 |
| 2 | PolyTHF-1000 | 97.7 (0.2 mol OH) | 87.0 (0.48 mol ester) | 18.2% | 2702 | 8157 |
| 3 | PolyTHF-250 | 25.0 (0.2 mol OH) | 80.0 (0.44 mol ester) | 16.2% | 2097 | 4131 |
| 4 | PolyTFH-250/DMA[1] | 75.0/39.2 (0.15 mol free OH) | 408 (0.23 mol ester) | 0.7% | 6265 | 15958 |
| 5 | CHDM/DMI/TMTM[2] | 28.8/4.85/12.61 (0.20 mol free OH) | 72.34 (0.4 mol ester) | 12.2% | 2058 | 6800 |
| 6 | CHDM/DMI/DMT[3] | 52.3/47.6/15.8 (0.074 mol free OH) | 20.1 (0.11 mol ester) | NA[4] | NA[4] | NA[4] |

[1]DMA = dimethyl adipate
[2]CHDM = cyclohexandedimethanol, DMI = dimethyl isophthalate, TMTM = trimethyltrimellitate
[3]DMT = dimethyl terephthalate
[4]Sample only partially soluble in ethyl acetate
[5]Determined by GPC, RI detection, polystyrene standards

EXAMPLE 3

A 250 mL high temperature polycondensation flask equipped with a short path distillation sidearm was charged with HBVE (hydroxybutylvinylether 87 g, 0.75 mol), dimethyl isophthalate (48.5 g, 0.25 mol) and titanium tetraisopropoxide catalyst (5 drops). The flask was fitted with a mechanical stirrer and vacuum applied (80 torr) (10.7 kPa.abs.). The mixture was stirred at 90° C. for six hours during which time methanol distilled from the reaction and the vacuum was lowered to 30 torr (4 kPa.abs.). GPC and HNMR analysis of the product indicated no acetal and 86% conversion to diester and 14% monoester. PolyTHF-1000 (BASF, 168 g, 0.17 mol) was added and the reaction continued at 120° C./<1 torr (0.13 kPa.abs.). Hydroxybutylvinyl ether distilled from the reaction. The mixture was cooled to room temperature and used without purification. FTIR indicate a trace of OH stretch and GPC (EtOAc solvent, RI detection) shows 6.3% free VEctomer ™ 4010. Molecular weights were calculated from the GPC data (RI detection) using polystyrene standards: $Mn = 4788$, $Mw = 14009$. HNMR analysis indicated no acetal formation. Again, the lack of acetals is highly desirable.

EXAMPLE 4

The procedures of Example 3 were repeated with different proportions of the starting materials with the results shown in the following table (including the results of Example 3).

TABLE B

| Vinyl Ether-Alcohol Used (mol OH) | Alcohol Used (mol OH) | Ester Used (mol ester) | % Free VEctomer ™ [3] 4010 | Mn[3] | Mw[3] |
|---|---|---|---|---|---|
| HBVE[1] (87 g, 0.75 mol OH) | PolyTHF-1000 (168 g, 0.34 | DMI[2] (48.5 g, 0.5 mol ester) | 6.3% | 4788 | 14009 |

TABLE B-continued

| Vinyl Ether-Alcohol Used (mol OH) | Alcohol Used (mol OH) | Ester Used (mol ester) | % Free VEctomer ™ [3] 4010 | Mn[3] | Mw[3] |
|---|---|---|---|---|---|
| HBVE (180 g, 1.55 mol OH) | PolyTHF-250 (60.2 g, 0.52 mol OH) | DMI (97 g, 1.0 mol ester) | 20.3% | 1702 | 2738 |

[1]HBVE = Hydroxybutylvinyl ether
[2]DMI = dimethyl isophthalate
[3]Determined by GPC, RI detection, polystyrene standards

EXAMPLE 5

A high temperature polycondensation flask equipped with a short path distillation sidearm was charged with polyTHF-250 (BASF, 108.9 g, OH#=476.9, g, 0.92 mol OH), dimethyl isophthalate (169.2 g, 1.74 mol ester) and dibutyl tin diacetate catalyst (0.35 g). The flask was fitted with a mechanical stirrer and vacuum applied (90 torr)(12 kPa.abs.). The mixture was stirred at 110° C. for six hours during which time 28.9 g (98% of theory) methanol was distilled from the reaction mass. The mixture was cooled to room temperature and used without further purification. FTIR indicates no detectable OH stretch.

To 193.2 g of stage 1 produce in the polymerization flask was added 117.3 g hydroxybutylvinyl ether (1.0 mol). Vacuum (50 torr)(6.7 kPa.abs.) was applied and the mixture was heated to 120° C. After 6 hours, 20.9 g distillate had been collected (97% of theory, 83% methanol). Vacuum was lowered to <1.0 torr (0.13 kPa.abs.) and excess HBVE removed by distillation. After 1.5 hours, 39.9 g HBVE had been collected (93% of theory). The reaction mass was cooled yielding a clear, viscous oil. Analysis of the product by FTIR, HNMR and CNMR indicated complete vinyl ether end capping and no acetal is detectable in the product.

The above procedure was used to prepare a series of vinyl ether end capped oligomers with varying molecular weight. Molecular weight control was achieved via controlling the starting DMI/THF-250 stoichiometry. Note that higher DMI concentrations result in higher content of DMI end capped with HBVE (DMI-VE). This is a result of previously unreacted DMI condensing with HBVE in the second step.

TABLE 1

| | Effect of Stoichiometry on Oligomer Molecular Weight | | | | |
|---|---|---|---|---|---|
| Sample | DMI used (mol) | THF-250 used (mol) | Oligomer $M_n$ | $M_w$ | % DMI-VE |
| A | 2.0 | 1.0 | 2756 | 3161 | 20.2 |
| B | 1.75 | 1.0 | 3079 | 3626 | 14.9 |
| C | 1.5 | 1.0 | 3455 | 4325 | 8.3 |

If the ratio of DMI to THF-250 was increased further, the molecular weight would be expected to decrease and eventually approach that of DMI-VE. Alternatively, if the ratio of DMI to THF-250 approaches 1.0/1.0 then the molecular weight increases until the resulting polymer has an unsuitable viscosity and reactivity. Thus, it is possible to adjust the molecular weight to obtain the desired properties for the intended end use.

EXAMPLE 6

Comparative

A 250 mL high temperature polycondensation flask equipped with a short path distillation sidearm was charged with HBVE (24.0 g, 0.21 mol), dimethyl isophthalate (77.70 g, 0.40 mol), butanediol (27.14 g, 0.3 mol) and dibutyl tin diacetate catalyst (2 drops). Vacuum (170 torr) (22.7 kPa.abs.) was applied to the reactor. The mixture was heated at 140° C. for three hours during which time methanol distilled from the reaction and the vacuum was slowly lowered to <1 torr (0.13 kPa.abs.). After heating an additional two hours the reaction was cooled to room temperature. HNMR analysis of the product indicated 25% of the vinyl ether groups had been converted to acetal. FTIR indicates no detectable OH stretch and GPC (EtOAc solvent, RI detection) shows a uniform product distribution. Molecular weights were calculated from the GPC data using polystyrene standard: Mn=1961, Mw=3130.

The product ester of dimethyl isophthalate and butanediol endcapped with hydroxy butyl vinyl ether was curable using cationic polymerization. However, the large amount of acetal reduced the vinyl ether functionality and thus would inhibit complete polymer network formation. The acetals would be expected to cleave under acid conditions and produce extractables in the cured polymer.

EXAMPLE 7

Comparative

A polymerization flask equipped with a nitrogen bubbler and magnetic stirrer was charged with hydroxy butyl vinyl ether (HBVE 50.65 g, 0.44 mol), dimethyl adipate (DMA 36.49 g, 0.1 mol) and lithium wire (0.0182 g, 0.05% based upon DMA) Nitrogen flow was started and the reaction mixture heated at 50° C. The reaction was followed by GC and nearly complete conversion to HBVE/DMA/HBVE was obtained in 3.5 hours. The reaction mixture was a clear, light brown oil. After cooling to room temperature, the product was washed with 2% aqueous $H_3PO_4$ and saturated aqueous NaCl. The product obtained was a clear, light yellow oil. The final product would not cure cationically without the aqueous washings. In addition, the washing step removes a portion of the color from the product. Residual catalyst inhibits the curing of the polymer by cationic polymerization.

EXAMPLE 8

Several of the oligomers produced in the previous examples were mixed with 0.5% iodonium catalyst (GE 479-2092C) and cured as 6 mil films on glass plates. A cure dose of 800 mj/cm² was used to ensure complete cure. No attempt to determine minimum cure dose was made. All of the films were tack-free and completely cured though. The cured films were analyzed by DMA to determine their glass transition temperatures. The results are as follows:

TABLE C

| Table A Test No. | Tg, °C. |
| --- | --- |
| 3 | 2° C. |
| 2 | −38° C. |
| 1 | −64° C. |
| 4 | too soft |

We claim:

1. A method of preparing vinyl ether terminated polyesters comprising the steps of:
   (a) reacting a polyol with a vinyl ether terminated polybasic ester in the presence of a transesterification catalyst to produce a vinyl ether terminated oligomer of said polyol and polybasic ester and as a by-product a hydroxy monovinyl ether, and
   (b) continuously separating said by product hydroxy monovinyl ether during the reaction of (a).

2. The method of claim 1 wherein said vinyl ether terminated polybasic ester is the reaction product of a polybasic ester and the hydroxy monovinyl ether of (b).

3. The method of claim 2 wherein said polybasic ester has the formula

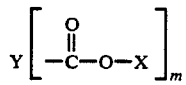

where
   Y is a radical having a molecular weight of 14 to above 500 and selected from the group consisting of alkylene, arylene, aralkylene and cycloalkylene radicals
   X is a radical selected from the group consisting of alkyl having 1 to 6 carbon atoms, arylene, and aralkylene
   m is 2 to 6.

4. The method of claim 2 wherein the hydroxy monovinyl ether has the formula

R'CH=CR"O—Z—OH

R' and R" are mono valent radicals selected from the group consisting of H and alkyl groups having 1–10 carbon atoms where
   Z is a divalent radical having a molecular weight of 28 to about 500 and selected from the group consisting of alkylene or cycloalkylene radicals 5. The method of claim 1 wherein said polyol has the formula A-(OH)

where n is 2 to 6,
   A is a radical selected from the group consisting of alkyl having 2 to 10 carbon atoms,
   polyesters,
   linear and cyclic ethers,
   arylene, or aralkylene 6. The method of claim 1 wherein said reaction is carried out at a temperature of about 50° to 250° C. and a vacuum of about 0.0133 to 66.7 kPa.abs.

7. The method of claim 1 wherein the mol ratio of said vinyl ether-terminated polybasic ester to said polyol is between about 1/20 to 20/1, excluding a ratio of exactly 1.0/1.0.

8. The method of claim 7 wherein said mol ratio is 1/5 to 5/1, excluding a ratio of exactly 1.0/1.0.

9. The method of claim 2 wherein said vinyl ether-terminated polybasic ester is the reaction product of dimethyl isophthalate and hydroxy butyl vinyl ether and said polyol is poly tetrahydrofuran.

10. A method of preparing vinyl ether terminated polyesters comprising the steps of:
    (a) reacting a polyol with a polybasic ester in the presence of a transesterification catalyst to produce a chain-extended oligomer of said polyol and poly basic ester and as a by-product an alcohol, continuously separating said alcohol during said reaction, and
    (b) capping the chain-extended oligomer of (a) by reaction with a hydroxy mono vinyl ether or vinyl ether terminated ester.

11. The method of claim 10 wherein said polybasic ester has the formula

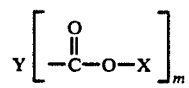

where
   Y is a radical having a molecular weight of 14 to above 500 and selected from the group consisting of alkylene, arylene, aralkylene and cycloalkylene radicals
   X is a radical selected from the group consisting of alkyl having 1 to 6 carbon atoms, phenyl, and substituted phenyl
   m is 2 to 6.

12. The method of claim 10 wherein said hydroxy monovinyl ether has the formula

R'CH=CR"O—Z—OH

R' and R" are mono valent radicals selected from the group consisting of H and alkyl groups having 1–10 carbon atoms where
   Z is a divalent radical having a molecular weight of 28 to about 500 and selected from the group consisting of alkylene or cycloalkylene radicals 13. The method of claim 10 wherein said polyol has the formula A-(OH)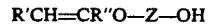

where n is 2 to 6,
   A is alkyl having 2 to 10 carbon atoms,
   polyesters,
   linear and cyclic ethers,
   arylene, or aralkylene 14. The method of claim 10 wherein said reaction is carried out at a temperature of about 50° to 250° C. and a vacuum of 0.0133 to 66.7 kPa.abs.

15. The method of claim 10 wherein the mol ratio of said polybasic ester to said polyol is between about 1/20 to 20/1, excluding a ratio of exactly 1.0/1.0.

16. The method of claim 10 wherein said mol ratio is 1/5 to 5/1, excluding a ratio of exactly 1.0/1.0.

17. The method of claim 10 wherein said polyol is polytetrahydrofuran, said polybasic ester is dimethyl isophthalate, and said hydroxy monovinyl ester is hydroxy butyl vinyl ether.

* * * * *